United States Patent
Scarola

(10) Patent No.: US 8,862,483 B2
(45) Date of Patent: Oct. 14, 2014

(54) DATA CAPTURE AND WORKFLOW MANAGEMENT TECHNIQUE

(75) Inventor: Todd Franklin Scarola, Crozier, VA (US)

(73) Assignee: General Electric Company, Schenectady, NY (US)

( * ) Notice: Subject to any disclaimer, the term of this patent is extended or adjusted under 35 U.S.C. 154(b) by 882 days.

(21) Appl. No.: 12/633,201

(22) Filed: Dec. 8, 2009

(65) Prior Publication Data

US 2011/0137671 A1   Jun. 9, 2011

(51) Int. Cl.
- *G06Q 10/00* (2012.01)
- *G06Q 50/00* (2012.01)
- *G06Q 10/10* (2012.01)
- *G06Q 10/06* (2012.01)
- *G06Q 50/22* (2012.01)

(52) U.S. Cl.
CPC .............. *G06Q 50/22* (2013.01); *G06Q 10/103* (2013.01); *G06Q 10/06* (2013.01)
USPC .................................. 705/2; 705/3

(58) Field of Classification Search
CPC ............................... G06Q 50/22; G06Q 50/24
USPC ........................................................... 705/2, 3
See application file for complete search history.

(56) References Cited

U.S. PATENT DOCUMENTS

| | | | |
|---|---|---|---|
| 7,996,465 B2 * | 8/2011 | Cromp et al. | 709/204 |
| 2004/0078169 A1 * | 4/2004 | Oba et al. | 702/186 |
| 2004/0138925 A1 * | 7/2004 | Zheng | 705/2 |
| 2005/0049017 A1 * | 3/2005 | Yoda | 455/575.1 |
| 2007/0129983 A1 * | 6/2007 | Scherpbier et al. | 705/8 |
| 2010/0164961 A1 * | 7/2010 | Horie et al. | 345/501 |
| 2010/0204999 A1 | 8/2010 | Scarola | |
| 2011/0234598 A1 | 9/2011 | Scarola et al. | |

* cited by examiner

*Primary Examiner* — Neha Patel

(57) ABSTRACT

Data capture and workflow management devices, systems, and methods are provided. In one embodiment, a system includes a data processing system having a processor and a storage device. The storage device may include application instructions encoded therein, and the application instructions may include a workflow engine to facilitate healthcare delivery to a patient. The system may further a data capture device to communicate data to the data processing system over a network. The data capture device may be provided in the form of a magnet board including a plurality of magnetic sensors to detect user-placement of a magnet within a region associated with a magnetic sensor.

7 Claims, 7 Drawing Sheets

DATA CAPTURE AND WORKFLOW MANAGEMENT TECHNIQUE

BACKGROUND

The present disclosure relates generally to the field of data capture and management. More specifically, the present disclosure relates to systems and methods for facilitating information collection and management of a workflow process, such as a clinical workflow process.

Healthcare facilities, such as hospitals and clinics, may implement various workflow processes to manage patient flow, quality of care, and other operational aspects of the facilities. For example, a hospital may have workflow processes for managing preoperative care, intraoperative care, and postoperative care for patients admitted for surgery. Additionally, other workflow processes may be used to manage other aspects of healthcare delivery, such as emergency room care, intensive care, or neonatal care, as well as to manage other aspects of the healthcare facility, such as preparation of an operation room for surgery. These various workflow processes may generally include steps to be completed by healthcare providers (e.g., doctors, nurses, and other people at a healthcare facility).

For instance, in a hospital, healthcare professionals may administer pharmaceuticals to patients, may routinely interact with patients for purposes of consultation, observation, and testing, may need to prepare patients for surgery, may need to prepare rooms to provide healthcare delivery, and so forth. In some instances, the healthcare professionals completing such tasks may make a written observation of the healthcare delivery event (e.g., on a patient chart) or may enter information about the event in a workstation remote from the patient. For example, a nurse may attend to numerous patients in sequence and may administer drugs to some of these patients. Subsequently, following interactions with the sequence of patients (e.g., at the end of a shift) the nurse may then enter records of which drugs and dosages were administered to which patients, which other tasks the nurse may have completed during his or her shift, and so forth. The entry of such records may be made through use of a software application on a terminal or workstation to facilitate such entry. In complex environments, however, such data capture may involve very targeted (and costly) user interfaces, and users may inadvertently enter incorrect data. Additionally, in some cases, the delay in data entry by healthcare professionals may also be undesirable.

BRIEF DESCRIPTION

There is a need for a system and method for capturing data during a workflow process, such as a healthcare delivery process. There is also a need to efficiently manage a workflow based on such data capture. Some embodiments described herein may be operable to address the needs and concerns described above. Certain aspects commensurate in scope with the originally claimed invention are set forth below. It should be understood that these aspects are presented merely to provide the reader with a brief summary of certain forms various embodiments of the invention might take, and that these aspects are not intended to limit the scope of the invention. Indeed, the invention may encompass a variety of aspects that may not be set forth below.

In accordance with one embodiment of the subject matter described herein, a system includes a data processing system, a communications network, and a data capture device. The data processing system may include a processor and a storage device including application instructions encoded in one or more computer-readable media for execution by the processor, wherein the application instructions include a workflow engine configured to facilitate healthcare delivery to a patient. The data capture device may be configured to communicate data to the data processing system via the communications network, wherein the data capture device comprises a magnet board including a plurality of magnetic sensors configured to detect placement of one or more magnets by a user on regions of the magnet board associated with the magnetic sensors.

According to another embodiment, a magnet board includes a magnetic substrate and a magnetic sensor positioned relative to the magnetic substrate and configured to detect the presence of a removable magnet magnetically coupled to the magnetic substrate at a location proximate the magnetic sensor. The magnet board may also include a data receiver configured to receive from the magnetic sensor data indicative of the presence or absence of the magnet at the location proximate the magnetic sensor. Further, the magnet board may include a data transmitter configured to output the magnetic sensor data from the magnet board to an external data processing system.

According to yet another embodiment, a method includes detecting a magnetic field of a magnet via a magnetic sensor of a data capture device. The method may further include communicating data from the data capture device to a data processing system programmed with a workflow engine to facilitate monitoring of steps of a clinical process of a healthcare provider. Additionally, the method may include associating via a software routine the detection of the magnetic field with completion of a milestone event associated with one or more of the steps of the clinical process, and outputting a report to a user indicative of the completion of the milestone event.

Various refinements of the features noted above may exist in relation to various aspects of the subject matter described herein. Further features may also be incorporated in these various aspects as well. These refinements and additional features may exist individually or in any combination. For instance, various features discussed below in relation to one or more of the illustrated embodiments may be incorporated into any of the above-described embodiments of the present invention alone or in any combination. Again, the brief summary presented above is intended only to familiarize the reader with certain aspects and contexts of the subject matter herein without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
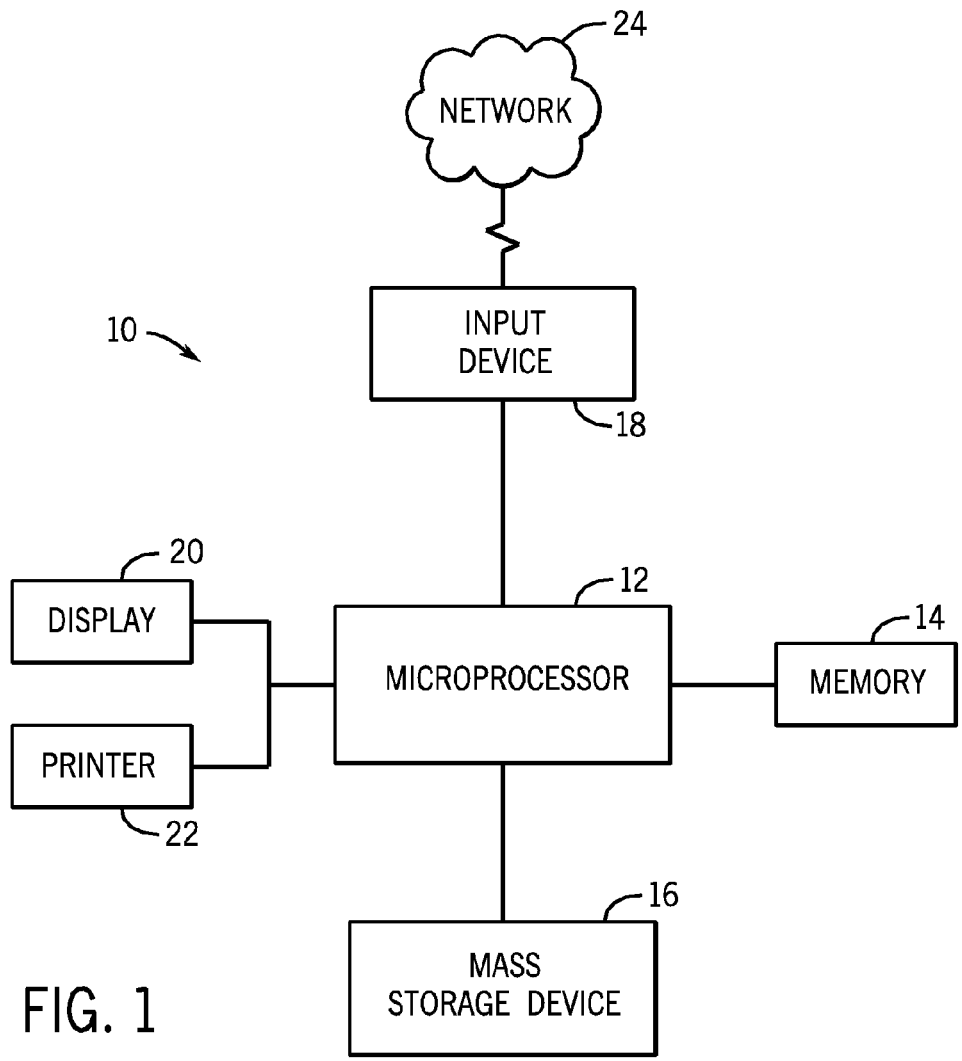
FIG. 1 is a block diagram of a processor-based device or system in accordance with one embodiment.

One or more specific embodiments of the presently disclosed subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed subject matter, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Certain embodiments of the present disclosure relate to a magnet board for capturing and managing milestone events in a clinical process. More particularly, in some embodiments, such a magnet board may include an overlay with human-readable indicia of various milestones in a healthcare delivery process that facilitate user interaction with the magnet board via user-manipulated magnets to indicate whether the milestones have been reached. The magnet board may also include magnetic sensors that detect whether magnets have been placed in certain regions of the magnet board, and the completion status of the milestone events may be determined from the presence or absence of such magnets from designated regions of the magnet board. Data collected from the magnet board may be transmitted to a data processing system to facilitate a workflow process based on the captured data. In some embodiments, the magnet board may be positioned at a point of patient care (e.g., on a patient bed, or in a patient bay or room) to facilitate and simplify data entry by a healthcare professional or other user, and a data processing system may enable use of the data beyond the point of patient care to drive a clinical workflow process.

Turning now to the drawings, and referring first to FIG. 1, an exemplary processor-based system 10 for use in conjunction with the subject matter described herein is depicted. The exemplary processor-based system 10 may be a general-purpose computer, such as a personal computer, configured to run a variety of software (e.g., application instructions), including software implementing all or part of the functionality described herein. Alternatively, the processor-based system 10 may include, among other things, a server, a distributed computing system, or an application-specific computer or workstation configured to implement all or part of the present technique based on specialized software and/or hardware provided as part of the system. Further, the processor-based system 10 may include either a single processor or a plurality of processors to facilitate implementation of the presently disclosed functionality.

In general, the exemplary processor-based system 10 may include a microcontroller or microprocessor 12, such as a central processing unit (CPU), which may execute various routines and processing functions of the system 10. For example, the microprocessor 12 may execute various operating system instructions as well as software routines configured to effect certain processes stored in or provided by a manufacture including one or more computer-readable storage media, such as a memory 14 (e.g., a random access memory (RAM) of a personal computer) or one or more mass storage devices 16 (e.g., an internal or external hard drive, a solid-state storage device, CD-ROM, DVD, or other storage device). In addition, the microprocessor 12 processes data provided as inputs for various routines or software programs, such as data provided as part of the present techniques in computer-based implementations.

Such data may be stored in, or provided by, the memory 14 or mass storage device 16. Alternatively, such data may be provided to the microprocessor 12 via one or more input devices 18. The input devices 18 may include manual input devices, such as a keyboard, a mouse, or the like. In addition, the input devices 18 may include a network device, such as a wired or wireless Ethernet card, a wireless network adapter, or any of various ports or devices configured to facilitate communication with other devices via any suitable communications network 24, such as a local area network or the Internet. Through such a network device, the system 10 may exchange data and communicate with other networked electronic systems, whether proximate to or remote from the system 10. The network 24 may include various components that facilitate communication, including switches, routers, servers or other computers, network adapters, communications cables, and so forth.

Results generated by the microprocessor 12, such as the results obtained by processing data in accordance with one or more stored routines, may be provided to an operator via one or more output devices, such as a display 20 and/or a printer 22. Based on the displayed or printed output, an operator may request additional or alternative processing or provide additional or alternative data, such as via the input device 18. Communication between the various components of the processor-based system 10 may typically be accomplished via a chipset and one or more busses or interconnects which electrically connect the components of the system 10.

Figure 2:
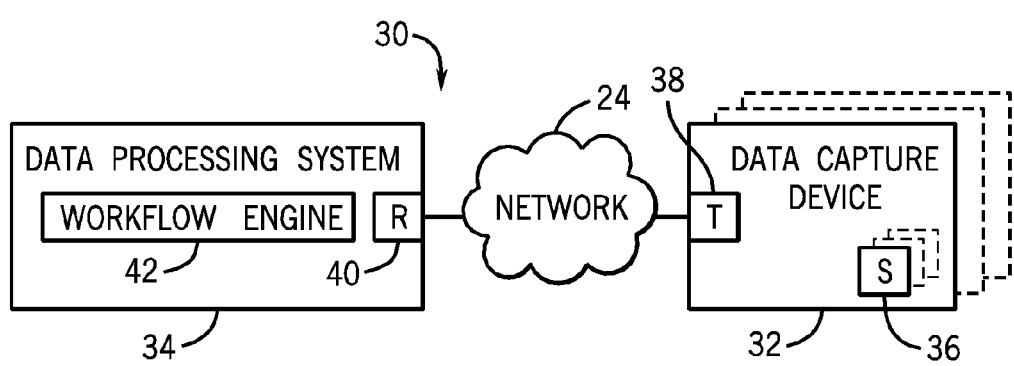
FIG. 2 depicts a networked system for capturing and processing data in accordance with one embodiment.

The processor based-system 10 may be configured to facilitate analysis of information from one or more data capture devices and to manage a workflow process based on such information, as generally described above. By way of example, a system 30 is depicted in FIG. 2 in accordance with one embodiment. In this presently illustrated embodiment, one or more data capture devices 32 are communicatively coupled to a data processing system 34 via the network 24. The data processing system 34 may include the processor-based system 10 illustrated in FIG. 1, although it is noted that in other embodiments the data processing system 34 may include various components or systems different than, or in addition to, those illustrated in FIG. 1. In one embodiment, the data processing system 34 may further include or be included in a location system (e.g., a "real-time" location system) for tracking objects (e.g., patients, personnel, medical or other equipment, etc.) within a region, such as within a hospital or other healthcare facility. Further, while the data capture devices 32 and the data processing system 34 may be discrete components as generally depicted in FIG. 2, it is noted that the data capture devices 32 may themselves include some or all of the data processing system 34 to facilitate the various functionalities described herein.

The data capture devices 32 include one or more sensors 36 configured to detect data capture events. For example, in some embodiments, the data capture devices 32 include magnet boards configured to receive magnets positioned thereon by users of the data capture devices 32 (e.g., healthcare professionals in the case of data capture devices 32 in a healthcare facility) and the sensors 36 include magnetic sensors, such as mechanical reed switches responsive to magnetic fields, configured to detect placement of such magnets on particular locations on the magnet boards. Particularly, in one embodiment, the sensors 36 may include mechanical reed switches distributed by Hamlin Electronics L.P. of Lake Mills, Wis., as part number MITI-3V1 6-12.5. The data capture devices 32 may also include transmitters 38 for outputting data from the data capture devices 32 to the data processing system 34 via the network 24 and one or more receivers 40. The data output from the data capture devices 32 may include data indicative of the states of the magnetic sensors 36, data generated by the data capture devices 32 based on such states, or the like. Further, in some embodiments the transmitters 38 and the receiver 40 may each be provided in the form of a transceiver enabling bidirectional communication, although unidirectional devices may also or instead be employed.

Additionally, in some embodiments, communication of data between the data capture devices 32 and the data processing system 34 may include wireless communication, such as by way of a wireless transmitter 38 and a wireless receiver 40. Wireless communication between the data capture devices 32 and the data processing system 34 may be effected through any suitable wireless communication protocol. For example, in one embodiment the data capture devices 32 may communicate with the data processing system 34 in accordance with the ZigBee communication standard. In other embodiments, however, communication may be in accordance with Bluetooth, WiFi, or other wireless communication standards. Still further, communication between the data capture devices 32 and the data processing system 34 may also or instead be provided via a wired connection.

The data processing system 34 may include various software routines (e.g., application instructions), such as a workflow engine 42, for analyzing data and managing processes based on such data. For example, in a healthcare context, the data processing system 34 may include the workflow engine 42 adapted to manage various processes of a healthcare facility, such as healthcare delivery processes. Further, in at least one embodiment, the workflow engine 42 is configured to manage one or more clinical processes based on data received from the data capture devices 32.

Figure 3:
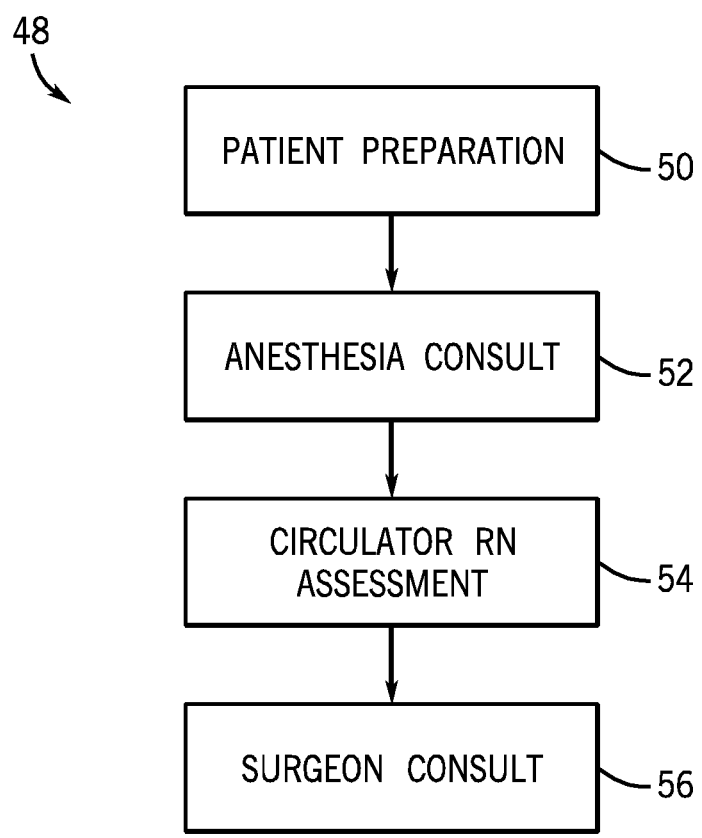
FIG. 3 is a flow diagram of an embodiment of a workflow process that may be facilitated via the system of FIG. 2.

For example, one such clinical process may include monitoring the completion of certain steps or milestones in preparing a patient for surgery in an operating room. Such a process 48 is generally illustrated in FIG. 3 in accordance with one embodiment. The process 48 may include a patient preparation step 50, an anesthesia consult step 52, a circulator registered nurse ("RN") assessment step 54, and a surgeon consult step 56. In other words, a workflow for determining whether a patient is ready to be moved from pre-operative care to surgery may include determining whether the patient has been made ready for surgery, whether the patient has received an anesthesia consultation, whether a registered nurse (or other) circulator has completed his or her assessment, and whether the patient has consulted with the surgeon. Although the steps 50, 52, 54 and 56 are depicted in a given order in FIG. 3, it will be appreciated these steps are provided merely by way of example and that these steps, or steps of other processes disclosed herein, may be performed in any suitable order.

Figure 4:
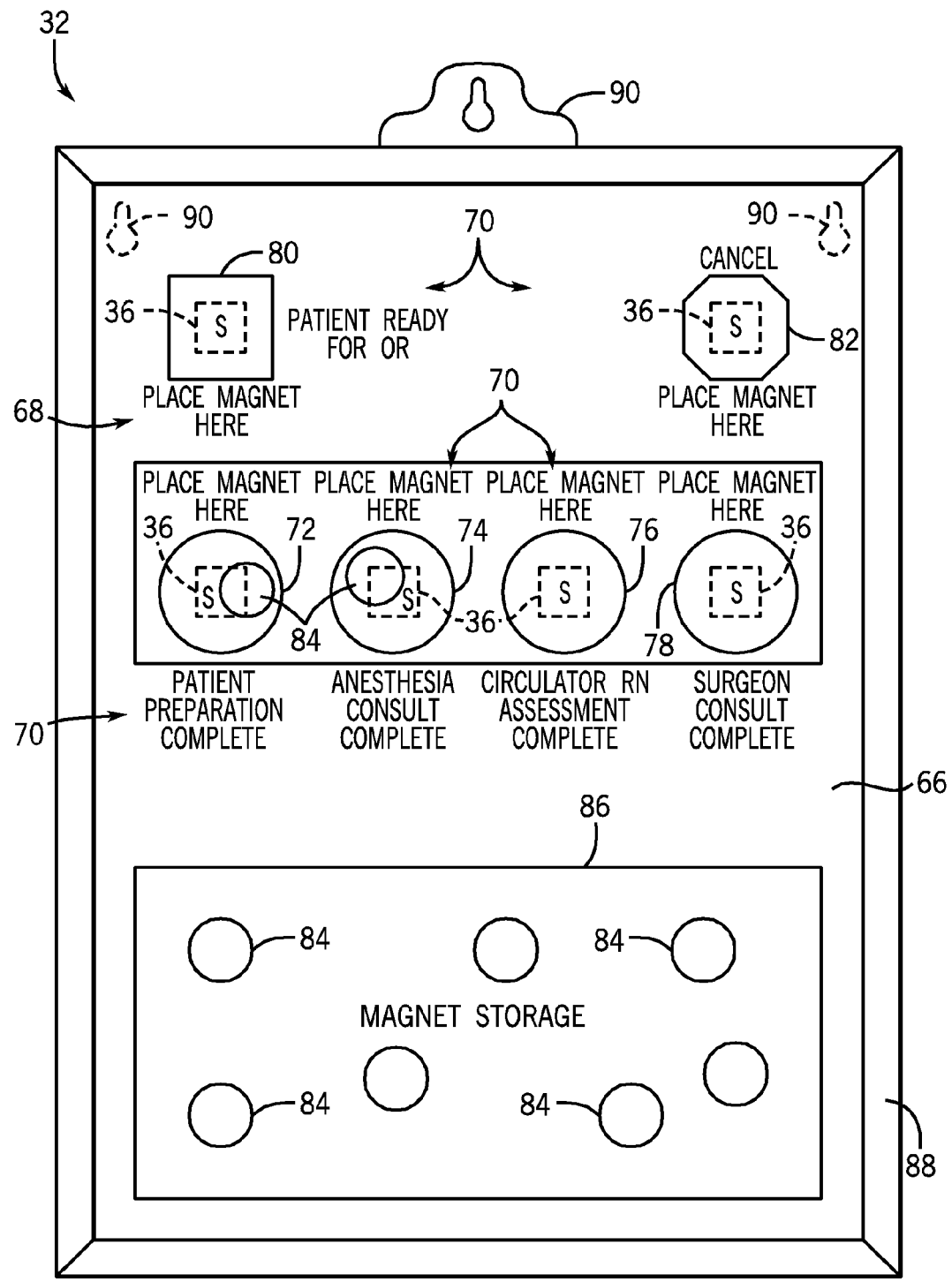
FIG. 4 illustrates a data capture device in the form of a magnet board in accordance with one embodiment.

An example of a data capture device 32 in the form of a magnet board 66 is generally depicted in FIG. 4 in accordance with one embodiment. In the presently illustrated embodiment, the magnet board 66 includes a printed overlay or template 68 on a front surface of the magnet board 66 for facilitating user interaction with the magnet board 66. The printed overlay 68 may include various printed human-readable indicia 70 that instruct a user, such as a healthcare professional, as to how to indicate that certain milestones in patient readiness have been reached. For example, in the depicted embodiment, the overlay 68 includes marked regions 72, 74, 76, and 78. Particularly, each of the regions 72, 74, 76, and 78 corresponds to a respective step 50, 52, 54 and 56 of the clinical process 48 depicted in FIG. 3. Further, each of the regions 72, 74, 76 and 78 may be provided proximate to (e.g., directly over) a respective magnetic sensor 36. The overlay 68 may also include additional regions 80 and 82 to facilitate user indications that a patient is ready for the operating room or that the workflow is to be cancelled, respectively. Each of these regions 80 and 82 may also be provided proximate a respective magnetic sensor 36.

Upon completion of various milestone events, such as those described above, a user may place a magnet 84 within one of the marked regions 72, 74, 76, and 78 to indicate that the milestone associated therewith has been reached. For instance, magnets 84 may be placed within regions 72 and 74 and the respective magnetic sensors 36 of these two regions may detect the presence of such magnets 84 (e.g., the magnetic field of such magnets 84 may alter the state of respective magnetic switches of the magnetic sensors 36). Accordingly, in one embodiment, an orderly or other healthcare professional may prepare a patient for surgery and indicate such completion by placing a magnet 84 within the region 72. Similarly, an anesthesiologist may consult with the patient and then indicate that this consultation has been completed by placing a magnet 84 within the region 74. Additionally, a circulator RN may make his or her assessment of the patient and indicate that such an assessment has been completed by placing a magnet 84 within the region 76, and a surgeon may consult with the patient and then indicate that the surgical consult is complete by placing a magnet 84 within the region 78. For each of these milestones, a respective magnetic sensor 36 may detect that a magnet 84 has been placed within the corresponding region of the overlay 68 and the current status of steps of a workflow process may thus be determined.

For example, in one embodiment, the magnet board 66 may communicate the status of each magnetic sensor 36 associated with the various regions (e.g., regions 72, 74, 76, 78, and the like) and the data processing system 34 may determine which milestone events have occurred based on such sensor status data. In another embodiment, the magnet board 66 may itself determine the status of the workflow milestones, such as via an internal processor implementing one or more data analysis routines, and may communicate such information to the data processing system 34 for recording or further processing. The overlay 68 may also include a magnet storage region 86 for receiving the magnets 84 that are not currently being used to activate one of the magnetic sensors 36. Further, in some embodiments the magnet board 66 includes a removable frame 88 to secure the overlay 68 to the magnet board 66. Additionally, the magnet board 66 may include one or more mounting features 90, such as tabs, straps, holes, and the like, to facilitate attachment of the magnet board 66 to a surface. Indeed, in other embodiments the magnet board 66 may be portable (such as attached to a clipboard) to enable mobile data capture.

Figure 5:
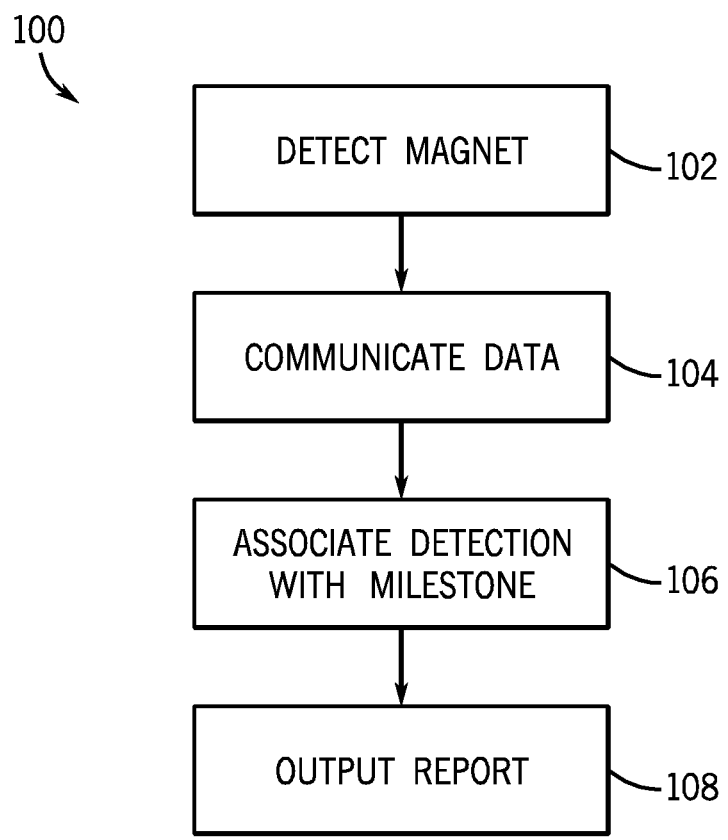
FIG. 5 is a flow diagram representative of operation of the system of FIG. 2 in accordance with one embodiment.
Figure 6:
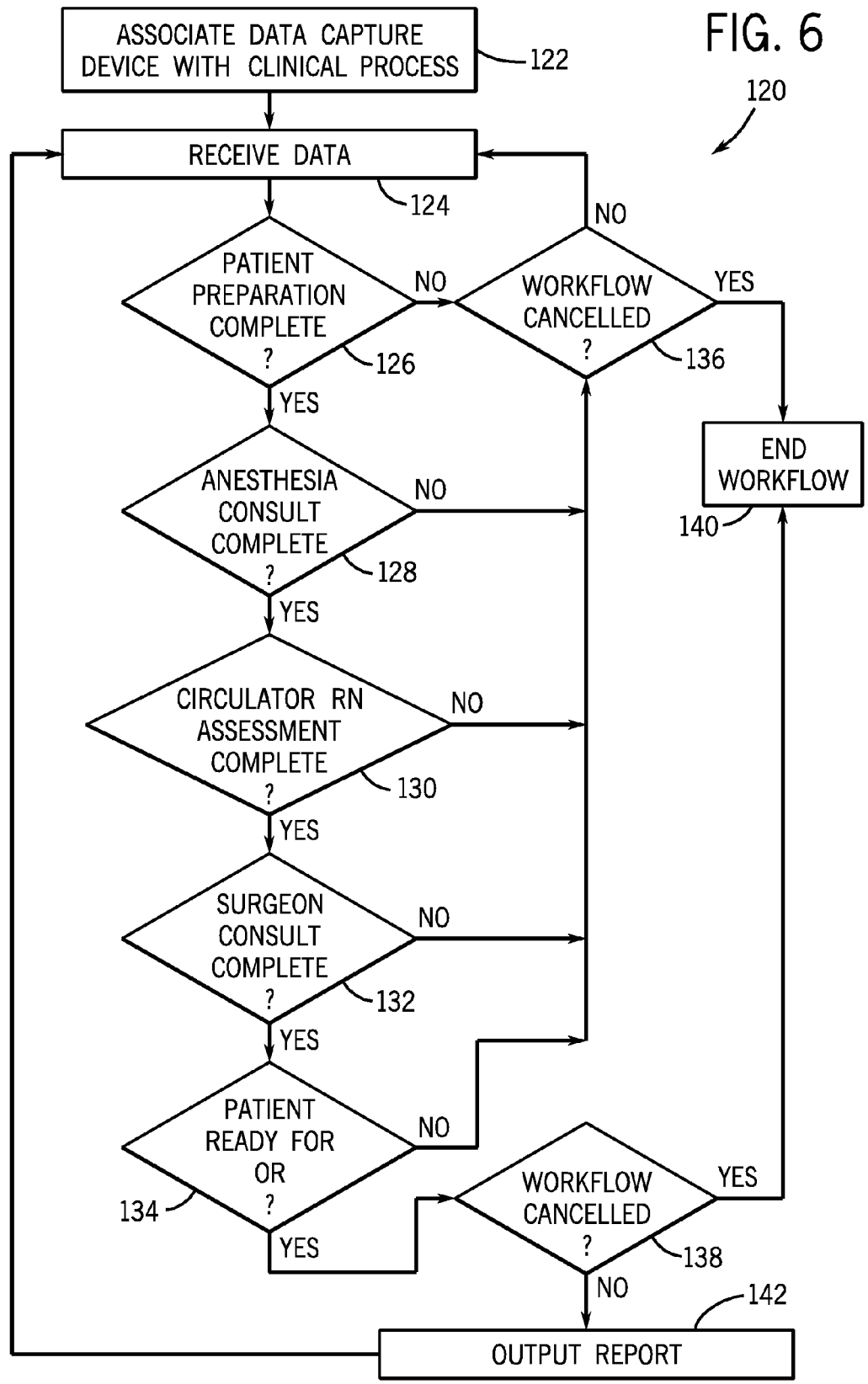
FIG. 6 is a flow diagram representative of operation of the system of FIG. 2 with respect to the workflow process of FIG. 3 in accordance with one embodiment.

Operation of the magnet board 66 may be better understood with reference to flow diagrams 100 and 120 depicted by way of example in FIGS. 5 and 6, respectively. As provided in FIG. 5, a magnet 84 may be detected within a region of the overlay 68 (e.g., region 74) by a magnetic sensor 36 in a step 102. Data based on the detection, such as data indicative of the state of the magnetic sensor 36, may be transmitted in a step 104 (e.g., from the magnet board 66 to the data processing system 34, or from the magnetic sensor 36 to an internal processor 12 of the magnet board 36). The detection of the magnet in step 102 may be associated with a particular workflow milestone in step 106. In one embodiment, the step 104 includes communicating state data of one or more magnetic sensors 36 from the magnet board 66 to the data processing system 34, which may include software routines for performing the association of step 106, which may include interpreting such state data with respect to completion of various milestones to drive a clinical workflow process such as that described above.

In a step 108, a report may be output to a user based on the association of the step 106. For example, the data processing system 34 may determine that each of the steps 50, 52, 54, and 56 of the clinical process 48 has been completed (e.g., based on the presence of a respective magnet in each of regions 72, 74, 76, and 78) and an indication of patient readiness for movement to an operating room may be reported to any desired healthcare personnel, such as personnel responsible for moving the patient to the operating room, the surgical team, and so forth. Further, reports provided in the step 108 may include indications of which aspects of the clinical process 48 (or other workflow process) have been completed, which aspects of the clinical (or other) process 48 have not been completed, a lapsed time since the last milestone was reached, or any other desired information. Further, such reports may be provided directly to interested parties via text messages, pages, or the like, may be provided to workstations (e.g., those including a display 20 or printer 22) accessible by such personnel, or may be stored for future review.

It is noted that the data capture devices 32 may be configured to facilitate data capture with respect to different workflow processes. Indeed, an individual data capture device 32 may be adaptable (e.g., through different overlays) to enable use of the data capture device 32 with these different workflow processes. Accordingly, with reference to FIG. 6, a magnet board 66 (or other data capture device 32) may be associated with a particular clinical process (e.g., process 48) in a step 122 to enable the activation of the magnetic sensors 36 of the magnet board 66 to be associated with the correct aspects of the particular clinical process (e.g., steps 50, 52, 54, and 56).

The data processing system 34 may receive data indicative of the state of the magnetic sensors 36 in a step 124. Based on the received data, the workflow engine 42 may determine whether patient preparation has been completed, whether anesthesia consultation has been completed, whether the circulator RN assessment has been completed, and whether the surgical consultation has been completed, as generally represented by decision blocks 126, 128, 130, and 132. A determination may then be made (decision block 134) as to whether the patient is ready for the operating room. In one embodiment, the workflow engine 42 may automatically determine that the patient is ready for the operating room upon detection that steps 50, 52, 54, and 56 have been completed. In another embodiment, the workflow engine 42 may only determine that the patient is ready for the operating room based on the activation of the magnetic sensor 36 associated with region 80 (FIG. 4) of the magnet board 66 (e.g., by placement of a magnet 84 within the region 80).

In the event that one or more of these milestones have not been reached, the data processing system 34 may continue to receive and process data regarding the clinical process 48 (e.g., state data for the magnetic sensors 36) at the step 124. Additionally, the workflow of the clinical process 48 may be cancelled by the data processing system 34, such as upon receipt of an indication that the magnetic sensor 36 of region 82 (FIG. 4) has been triggered (decision blocks 136 and 138). If the workflow is cancelled, the workflow may end as depicted in FIG. 6 at block 140. If, however, the workflow has not been cancelled and each of the milestones associated with decision blocks 126, 128, 130, 132, and 134 have been reached, the data processing system 34 may determine that the patient is ready for the operating room and may output a report in a step 142.

Figure 7:
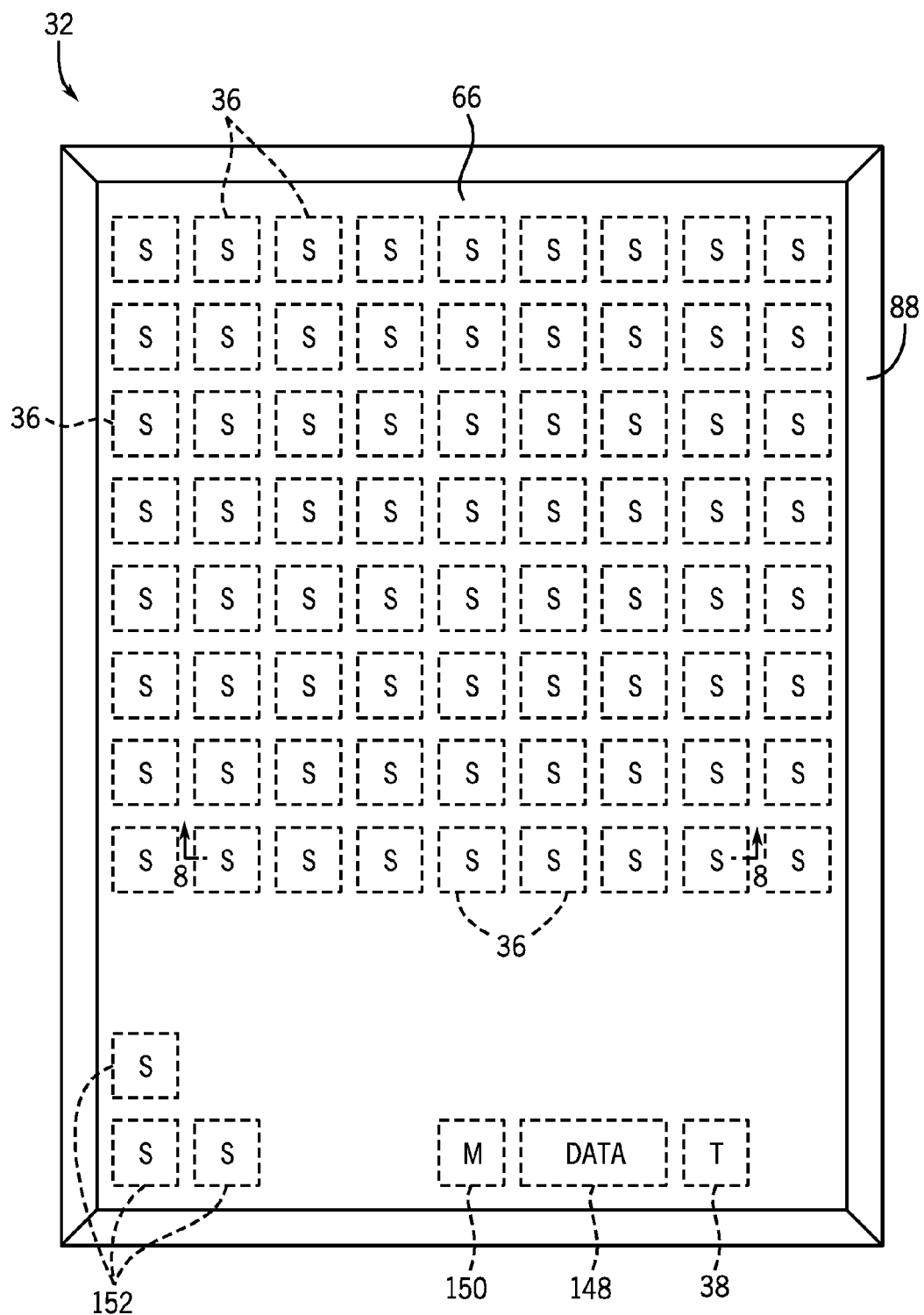
FIG. 7 is a diagrammatical representation of example components of a magnet board for capturing data in accordance with one embodiment.

Although the embodiment depicted in FIG. 4 illustrates only six magnetic sensors 36, it is noted that the magnet board 66 may include any number of such sensors to facilitate data capture and that the present techniques are not limited to the magnet board configuration depicted in FIG. 4. For example, in one embodiment generally depicted in FIG. 7, the magnet board 66 may include an array of magnetic sensors 36 for detecting the placement of magnets to indicate completion of milestone events in a workflow process. Additionally, the magnet board 66 may include one or more components 148 (e.g., a data receiver, a multiplexer, and a battery) for receiving and processing data from the magnetic sensors 36 and outputting such data via the transmitter 38. In some embodiments, the one or more components 148 may also identify the location of an activated magnetic sensor 36 with respect to the sensor array, and indicate the location of the activated sensor 36 (e.g., third row, second column) to the data processing system 34. Still further, in one embodiment, the magnet board 66 may include a memory device 150 for storing data received from the magnetic sensors 36. For instance, such storing of data from the magnetic sensors 36 may enable subsequent retrieval of data from the magnet board 66.

Additional magnetic sensors 152 may be provided along one or more edges of the magnet board 66 or at some other location, and may be reserved for purposes other than workflow process data capture (e.g., for special addressing to expand the functionality of the magnet board 66). For example, in one embodiment the magnet boards 66 may be modular such that milestones for a given clinical process may be divided over multiple magnet boards 66 (e.g., an array of magnet boards 66 to generally form a larger magnet board surface, or a distributed set of magnet boards 66). The additional magnetic sensors 152 may allow a user to identify the location of a particular magnet board 66 within a facility, to identify the relationship of the particular magnet board 66 with respect to other magnet boards 66 (e.g., each additional magnetic sensor 152 may be associated with a position within an ordered sequence of magnet boards 66), or the like.

Figure 8:
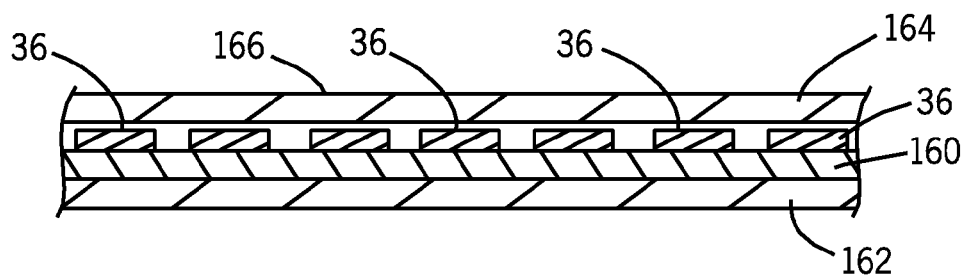
FIG. 8 is a generalized cross-sectional representation of the magnet board of FIG. 7 in accordance with one embodiment.
Figure 9:
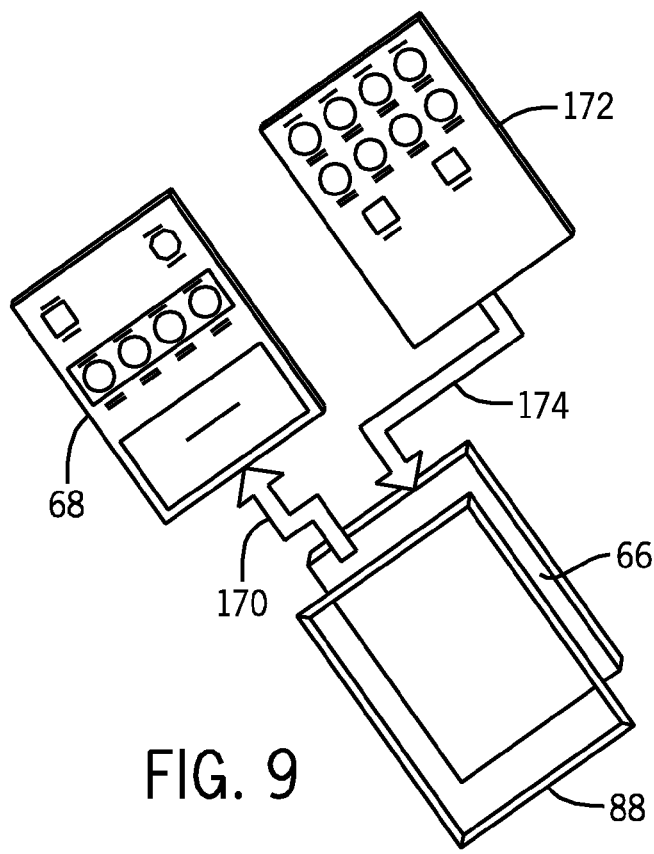
FIG. 9 illustrates the use of multiple overlays to facilitate different workflow processes with a magnet board in accordance with one embodiment.

FIG. 8 is representative of certain layers of the magnet board 66 in accordance with one embodiment. The magnet board 66 may generally include a metallic layer 160, such as a metallic mesh material, positioned between outer layers 162 and 164 of the magnet board 66 to allow the magnets 84 to be magnetically coupled to the magnet board 66. The overlay 68 may be placed over an outer surface 166 of the magnet board, and one or more of the magnetic sensors 36 may detect placement of one or more of the magnets 84 proximate to such sensors 34 (e.g., within one or more regions 72, 74, 76, et seq.) to facilitate data capture in accordance with the presently disclosed techniques. It is noted, however, that the magnet board 66 may be constructed in any suitable manner and may differ from the construction depicted in FIG. 8.

Additionally, in one embodiment, the magnet board 66 includes a removable frame 88 to allow the removal of the overlay 68, as generally indicated by arrow 170, and for receiving a different overlay 172, as indicated by arrow 174. Notably, the magnet board 66 may receive any number of different overlays associated with one or more clinical processes. For example, the overlay 68 may generally facilitate data capture of milestone events in patient readiness before surgery (e.g., in pre-operative care), while another overlay (e.g., the overlay 172) may facilitate data capture regarding milestone events of another process, such as that concerning a patient following surgery (e.g., in post-operative care). Consequently, the magnet board 66 may operate in conjunction with the data processing system 34 to facilitate data capture and management of any number of clinical processes in a healthcare facility. In one embodiment, the magnet board 66 is configured to receive overlays of a standard size (e.g., 8.5-inch×11-inch, A4, etc.), and the various overlays (including, for example, the overlays 68 and 172) may be printed on such standardized paper. Further, the design of these various overlays (e.g., 68 and 172) may be customized based on user preferences. Multiple magnet boards 66 may be used in conjunction with the data processing system 34 to simultaneously capture data pertaining to different workflow processes. Additionally, while certain embodiments are described herein with respect to healthcare delivery and processes, it is noted that the use of the present techniques in fields other than healthcare is also envisaged. Indeed, the present techniques are generally applicable to any of numerous other areas in which one or both of efficient data capture and workflow management are desirable.

In some embodiments, technical effects of the present subject matter may include, among others, efficient point-of-use milestone data capture and workflow management for clinical processes. Further, another technical effect may include the creation of a highly flexible data capture interface that may be tailored to specific workflow processes via interchangeable templates on the face of the data capture device. Still further, an additional technical effect may include enabling real-time notification of milestone event data of a distributed workflow process.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system comprising:
a data processing system including: a processor; and a storage device including application instructions encoded in one or more computer-readable media for execution by the processor, wherein the application instructions include a workflow engine configured to facilitate management of one or more workflow steps during healthcare delivery to a patient; wherein the steps of the workflow process correspond to activities performed by various personnel of a healthcare facility as part of a treatment administered to or performed on a patient;
a communications network; and
a data capture device comprises:
a magnet board including a plurality of magnetic sensors configured to detect placement of plurality removable magnets on regions of the magnet board associated with the magnetic sensors when a user places a respective removable magnet on the magnet board; and a removable template with indicia corresponding to locations of some or all of the magnetic sensors and each representing a respective step of the one or more workflow steps, wherein the removable template is positioned on a front surface of the magnet board so as to be visible to the users when the users place or remove magnets on the magnet board;
wherein the data capture device is configured to communicate the state of one or more magnetic sensors of the plurality of magnetic sensors to the data processing system;
wherein the application instructions of the data processing system include routines to receive an indication of an active state of the plurality magnetic sensors and associate the active state with completion of a healthcare delivery event and drive the workflow engine in response to activation of multiple magnetic sensors of the plurality of magnetic sensors indicative of a plurality of healthcare delivery events.

2. The system of claim 1, wherein the communications network includes a wireless communication network.

3. The system of claim 2, wherein the data capture device includes a wireless transmitter configured to transmit data via the wireless communications network.

4. The system of claim 1, comprising a real-time location system configured to facilitate tracking of at least one of patients or medical equipment within a healthcare facility.

5. The system of claim 4, wherein the real-time location system includes the data processing system.

6. The system of claim 1, comprising an additional data capture device configured to communicate additional data to the data processing system via the communications network, wherein the additional data capture device comprises an additional magnet board including an additional plurality of magnetic sensors configured to detect placement of one or more additional magnets on regions of the additional magnet board associated with the additional magnetic sensors, wherein the data processing system is configured to associate the additional data capture device with a clinical process different than that associated with the data capture device.

7. The system of claim 1, wherein the magnetic sensor includes a reed switch configured to switch in the presence of an applied magnetic field from the magnet.

* * * * *